(12) United States Patent
Liu et al.

(10) Patent No.: US 12,027,261 B2
(45) Date of Patent: Jul. 2, 2024

(54) WEARABLE DEVICES UTILIZING BONE CONDUCTION MECHANISMS

(71) Applicant: 5th Social Media Technology Inc., Los Angeles, CA (US)

(72) Inventors: Xiao Liu, Shanghai (CN); Eric Yuansuo Schee, Shanghai (CN); Chien Lin, Rancho Santa Fe, CA (US); Vincent Chen, Los Angeles, CA (US)

(73) Assignees: Xiao Liu, Rancho Santa Fe, CA (US); Eric Schee, Rancho Santa Fe, CA (US); Chien Lin, Rancho Santa Fe, CA (US)

( * ) Notice: Subject to any disclaimer, the term of this patent is extended or adjusted under 35 U.S.C. 154(b) by 335 days.

(21) Appl. No.: 17/243,191

(22) Filed: Apr. 28, 2021

(65) Prior Publication Data

US 2022/0139542 A1  May 5, 2022

(51) Int. Cl.
*G16H 40/63* (2018.01)
*G06F 1/16* (2006.01)
*G16H 50/20* (2018.01)

(52) U.S. Cl.
CPC ............ *G16H 40/63* (2018.01); *G06F 1/163* (2013.01); *G16H 50/20* (2018.01)

(58) Field of Classification Search
CPC ........ G16H 40/63; G16H 50/20; G16H 40/67; G06F 1/163; G06F 3/011; G06F 3/04883; G06F 3/167; H04R 1/083; H04R 2420/07; H04R 2460/13; H04R 1/028
See application file for complete search history.

(56) References Cited

U.S. PATENT DOCUMENTS

| 5,902,167 | A | * | 5/1999 | Filo | G10K 15/04 426/104 |
| 2002/0009972 | A1 | * | 1/2002 | Amento | G06F 3/011 455/66.1 |
| 2006/0104456 | A1 | * | 5/2006 | Filo | A61C 17/221 381/124 |

(Continued)

FOREIGN PATENT DOCUMENTS

| GB | 2470279 A | * | 11/2010 | ............. G11B 33/06 |
| JP | 2016130985 A | * | 7/2016 | |

OTHER PUBLICATIONS

Bone Conduction Communication: Research Progress and Directions by Maranda McBride, Phuong Tran, and Tomasz Letowski US Army Research Laboratory (Year: 2017).*

*Primary Examiner* — Alexandru Cirnu
(74) *Attorney, Agent, or Firm* — MagStone Law, LLP; Enshan Hong

(57) ABSTRACT

According to one or more aspects of the present disclosure a wearable oral device is provided. The wearable oral device may include a mouthpiece; a bone conduction component; and a processing device. The processing device may detect one or more user interactions by a first user with the wearable oral device; and perform one or more operations in view of the one or more user interactions. The one or more user interactions may include a user interaction by the first user with the mouthpiece. The one or more operations may include presenting a content item via the bone conduction component of the wearable oral device. The content item may include audio content. In some embodiments, the content item comprises a voice message from a second user.

16 Claims, 8 Drawing Sheets

(56) References Cited

U.S. PATENT DOCUMENTS

| | | | |
|---|---|---|---|
| 2009/0208031 A1* | 8/2009 | Abolfathi | H04R 1/1091 |
| | | | 381/74 |
| 2017/0070797 A1* | 3/2017 | Spector | A63B 71/085 |
| 2019/0045298 A1* | 2/2019 | Klemme | G10L 21/0208 |
| 2019/0332834 A1* | 10/2019 | Yeh | G06K 19/0702 |
| 2019/0387998 A1* | 12/2019 | Garten | A61M 21/00 |

* cited by examiner

WEARABLE DEVICES UTILIZING BONE CONDUCTION MECHANISMS

CROSS-REFERENCE TO RELATED APPLICATION

This application claims priority to Chinese Patent Application No. 202011200656.X, filed Oct. 30, 2020, the entire contents of which are herein incorporated by reference in their entirety.

TECHNICAL FIELD

This disclosure relates to the field of computing devices and related software applications and, in particular, to a wearable device utilizing bone conduction mechanisms.

BACKGROUND

Wearable devices may refer to electronic devices worn by users. Smartwatches, activity trackers, and other such wearable devices are becoming increasingly popular. Some wearable devices may have biometric tracking capabilities. For example, an existing wearable device may implement healthcare applications to measure the blood alcohol content of a user, a blood pressure of the user, calories burned by the user, etc.

BRIEF DESCRIPTION OF THE DRAWINGS

The present disclosure is illustrated by way of example, and not by way of limitation, in the figures of the accompanying drawings.

DETAILED DESCRIPTION

Figure 1:
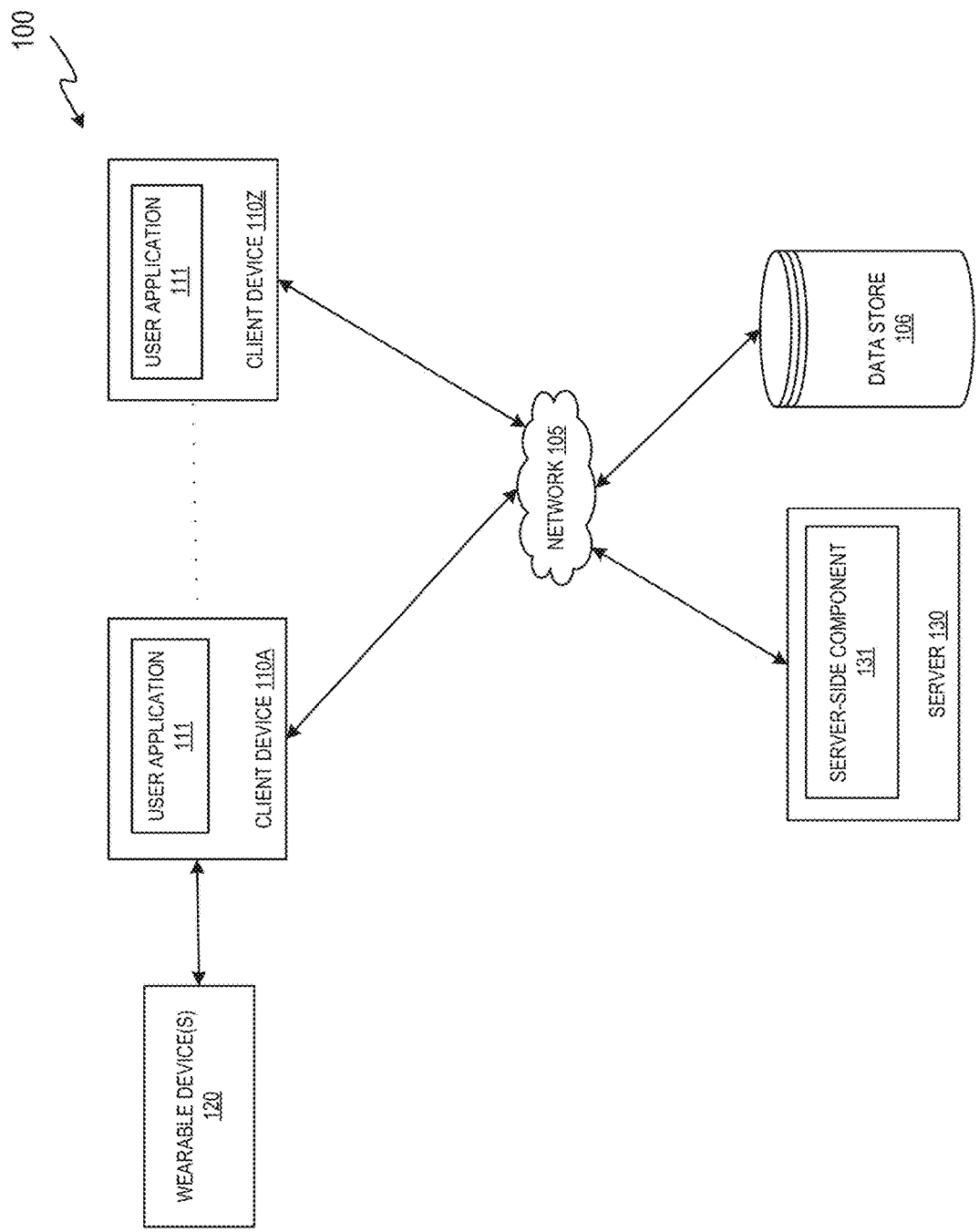
FIG. 1 illustrates an example of a system architecture for implementing a wearable device utilizing bone conduction mechanisms in accordance with some implementations of the disclosure.

Aspects and implementations of the present disclosure provide for a wearable device utilizing bone conduction mechanisms. As referred to herein, "wearable device" may refer to a device that may be attached to any portion of a user's body. The wearable device may include one or more components that are suitable for being placed in a user's mouth. For example, one or more portions of the wearable device may be coated by one or more edible materials (e.g., chocolate, candy, ice cream, ice, etc.). As another example, the wearable device may be and/or include an electronic cigarette, a toothbrush, and/or any other suitable device that includes a mouthpiece that may be positioned in a user's mouth. The wearable device may also be referred to as "wearable oral device" herein.

The wearable oral device may include a bone conduction component that may facilitate transmission of sound via bone conduction. While one or more portions of the wearable oral device (e.g., a portion of the wearable oral device that is coated with edible materials, the mouthpiece) are positioned in the user's mouth, the wearable oral device may present media content to the user via the bone conduction component. For example, the wearable oral device may present audio content (e.g., a song, a voice message, audio content of a video clip) via the bone conduction component. As such, the user may consume (e.g., watch, view) the media content while enjoying the edible materials on the wearable oral device or using the electronic cigarette in the wearable oral device. Furthermore, the wearable oral device can enable the user to consume the media content in a private manner given that the audio content played via the bone conduction component may be inaudible or approximately inaudible to outsiders.

As used herein, "media content" may include audio content, video content, images, graphics, and/or any other suitable content. As used herein, "media," "media item," "online media item," "digital media," "digital media item," "content," and "content item" can include an electronic file that can be executed or loaded using software, firmware or hardware configured to present the digital content item to a user.

In some embodiments, the wearable oral device may be connected to a mobile device to provide social networking, messaging, content sharing, voice and/or video calls, mapping, searching, navigation, and/or any other suitable functions. For example, a user application on the mobile device may detect the presence of the wearable oral device (e.g., by detecting one or more wireless signals transmitted by the wearable oral device). The user application may then present media content to the user using the wearable oral device and/or the mobile device. More particularly, for example, the user application may cause audio content to be presented to the user via the bone conduction component of the wearable oral device (e.g., by transmitting instructions for presenting the audio content via the bone conduction component). The user application may also present media content on a display of the mobile phone. For example, the user application may present video content related to the audio content on the display. As another example, the user application may present one or more user interfaces for controlling the playback of the audio content via the bone conduction component of the wearable oral device. As still another example, the user application may present one or more user interfaces for presenting a list of content items that may be consumed, shared, viewed, etc. by the user.

As another example, the user application may enable communications and/or interactions between the user and/or one or more other users. More particularly, for example, while a first user is interacting with the wearable oral device (e.g., by consuming the edible materials, issuing a voice command, entering a text input), the user application may identify one or more other users that are related to the first user and may present content to facilitate communications between the first user and the identified one or more other users. As a more particular example, the user application may detect one or more nearby users (e.g., by determining that computing devices of the nearby users are within a predetermined proximity to the mobile phone of the first user). The user application may prompt the first user to interact with the nearby users (e.g., by playing audio content including the prompt via the bone conduction component of the wearable oral device, presenting one or more user interfaces on the display of the mobile device of the first user). As another more particular example, the user application may facilitate the exchange of voice messages between the first user and a second user related to the first user (e.g., a social contact of the first user). For example, the user application may cause a voice message from the second user to be played via the wearable oral device (e.g., by sending data for playing the voice message via the bone conduction component to the wearable oral device).

FIG. 1 illustrates an example of a system architecture 100 for implementing a wearable device utilizing bone conduction mechanisms in accordance with some implementations of the disclosure. The system architecture 100 may include client devices 110A through 110Z, one or more wearable devices 120, a network 105, a data store 106, and a server 130. In one implementation, network 105 may include a public network (e.g., the Internet), a private network (e.g., a local area network (LAN) or wide area network (WAN)), a wired network (e.g., Ethernet network), a wireless network (e.g., an 802.11 network or a Wi-Fi network), a cellular network (e.g., a Long Term Evolution (LTE) network), routers, hubs, switches, server computers, and/or a combination thereof.

In one implementation, the data store 106 may be a memory (e.g., random access memory), a cache, a drive (e.g., a hard drive), a flash drive, a database system, or another type of component or device capable of storing data. The data store 106 may also include multiple storage components (e.g., multiple drives or multiple databases) that may also span multiple computing devices (e.g., multiple server computers). The data store 106 may store data that may be used to implement the embodiments of the present disclosure, such as media content, content items, etc.

The client devices 110A through 110Z may each include computing devices such as personal computers (PCs), laptops, mobile phones, tablet computers, netbook computers, wearable computing devices (e.g., smartwatches, eyeglasses, activity trackers, etc.), etc. In some implementations, client device 110A through 110Z may also be referred to as "user devices." Each of the client devices 110A through 110Z may be and/or include one or more computing devices 700 of FIG. 7.

Each client device may include a user application 111. In one implementation, the user application 111 may be a standalone application that may perform functions for implementing various embodiments of the present disclosure. In another implementation, the user applications 111 may include a web browser that can access, retrieve, present, and/or navigate content (e.g., web pages such as Hyper Text Markup Language (HTML) pages, digital media items, etc.) served by a web server. The user application 111 may also display an embedded media player (e.g., a Flash® player or an HTML5 player) that is embedded in a web page.

In some embodiments, the user applications 111 may be provided to the client devices 110A through 110Z by the server 130. For example, the user applications 111 may be applications that are downloaded from the server 130. As another example, the user applications 111 may include embedded media players that are embedded in web pages provided by the server 130.

The server 130 may be and/or include one or more computing devices (e.g., a rackmount server, a server computer, etc.) that are capable of performing functions in accordance with the embodiments of the present disclosure, such as performing searches based on search queries, identifying users related to each other, identifying media content related to one or more users, etc. In some embodiments, the server 130 may be and/or include one or more computing devices 700 of FIG. 7.

Each wearable device 120 may include one or more components that are suitable for being placed in a user's mouth. The wearable device 120 may be and/or include a wearable oral device 200 as described in connection with FIG. 2 below. In some embodiments, one or more portions of the wearable oral device 120 may be coated by one or more edible materials (e.g., chocolate, candy, ice cream, ice, etc.). In some embodiments, the wearable oral device 120 may be and/or include an electronic cigarette, a toothbrush, a pacifier, a bottle with straw, a mouthguard, eating utensils (e.g., a spoon, fork, knife, chopsticks), and/or any other suitable device that includes a mouthpiece that may be positioned in a user's mouth.

The wearable oral device 120 may include a bone conduction component that may facilitate transmission of sound via bone conduction. While one or more portions of the wearable oral device 120 (e.g., the portion coated with the edible materials, the mouthpiece) are positioned in the user's mouth, the wearable oral device may present media content to the user via the bone conduction component. For example, the wearable oral device 120 may present audio content (e.g., a song, a voice message) via the bone conduction component. As such, the user may consume the media content while enjoying the edible materials on the wearable oral device, using the electronic cigarette in the wearable oral device 120, and/or interacting with the wearable oral device 120 in any other suitable manner.

In some embodiments, the wearable oral device 120 may detect that one or more portions of the wearable oral device 120 are positioned in a user's mouth (e.g., by detecting a pressure applied to the wearable oral device 120 by the user's mouth, detecting a change in temperatures using a sensor coupled to the wearable oral device 120). The wearable oral device 120 may perform one or more operations in view of the detection. For example, the wearable oral device 120 may generate one or more signals indicating the detection. The signals may also include data collected by one or more sensors coupled to the wearable oral device 120. The wearable oral device 120 may further transmit the signals to a user device 110. As another example, the wearable oral device 120 may analyze the data collected by one or more sensors to check the temperature of the user (e.g., an oral temperature), check the oral health of the user, and/or perform any other suitable operations.

In some embodiments, one or more wearable oral devices may implement a scheduling application. For example, each of a plurality of wearable oral devices 120 may be associated with a user waiting for a service and/or product provided by a business (e.g., a restaurant, parking facility, hospital, store). The wearable oral devices 120 may be communicatively connected to the server 130 and/or any other suitable computing device. The server 130 may generate a queue representing a waiting list of the users. An element of the queue may correspond to a respective user waiting for the service and/or product. The server 130 may send a notification (e.g., a voice message) to a wearable oral device to notify the user of a queue position (e.g., the second inline), an expected waiting time, a queue status (e.g., waiting), a status of an order (e.g., ready for pickup), and/or any other suitable information about the queue. The notification may alert the user that it is the user's turn and/or that the product and/or service is ready to be provided to the user.

In some embodiments, one or more wearable oral devices may be used to enhance user experience in a social event and promote participants' engagement in the social event. Examples of the social event may include a show, concert, party, etc. In one implementation, certain audio content (e.g., audio effects, etc.) may be played via the wearable device in a social event (e.g., a show presented in an amusement park). In another implementation, a first wearable oral device may detect the presence of one or more other wearable oral devices (e.g., by determining that devices of the same type are within a predetermined proximity to the first wearable oral device). The wearable oral devices may then present certain media content (e.g., a predetermined song or image), illuminate light-emitting devices associated with the wearable oral devices, and/or perform any other suitable operations.

In some embodiments, the wearable oral device 120 may implement proximity-based applications. For example, when a user interacts with the wearable oral device 120 near a point of interest, the wearable oral device 120 may determine that the wearable oral device 120 is within a predetermined proximity to the point of interest and may present media content relating to the point of interest (e.g., audio content introducing the point of interest, audio content prompting the user to interact with the point of interest, etc.). The point of interest may be, for example, furniture, an art piece or any other object presented in a museum or any other location, a store, a bus stop, a building, etc. In one implementation, a transmitter positioned at the point of interest may broadcast a message including an identifier of the transmitter (e.g., a universally unique identifier) periodically. When the wearable oral device 120 is within a predetermined proximity to the transmitter, the wearable oral device 120 may detect the broadcast of the identifier of the transmitter and may perform suitable operations accordingly. For example, the wearable oral device 120 may send the identifier of the transmitter to another computing device (e.g., the server 130, a user device 110). The computing device may identify media content associated with the identifier of the transmitter and transmit the identified media content to the wearable oral device 120 for presentation. In some implementations, the message broadcasted by the transmitter positioned at the point of interest may also include an identifier of the media content (e.g., a uniform resource identifier of the media content). The wearable oral device 120 may retrieve the media content associated with the point of interest using the identifier of the media content (e.g., by sending a request for the media content to a server, retrieving media content associated with the identifier from a storage device, etc.).

In some embodiments, one or more portions of the media content related to the point of interest may also be presented by a user device associated with the user (e.g., a mobile phone). For example, when the user interacts with the wearable oral device 120 near the point of interest, the user device 110 may present media content introducing the point of interest or other media content related to the point of interest. As another example, the user device may present one or more user interfaces on a display of the user device to prompt the user to interact with the point of interest and/or the media content associated with the point of interest. More particularly, for example, the user interfaces may include a playlist of content items related to the point of interest (e.g., a video clip, audio clip, etc.). Upon receiving a user selection of one or more of the content items, the user device may cause the selected content items to be presented by the user device and/or the wearable oral device 120.

In some embodiments, while a first user is interacting with the wearable oral device 120, the wearable oral device 120 may be connected to a user device of the first user to provide social networking, messaging, content sharing, voice and/or video calls, mapping, searching, navigation, and/or any other suitable functions. For example, a user application 111 running on the user device of the first user may present media content to the first user upon detecting the presence of the wearable oral device 120. The user application 11 may detect the presence of the wearable oral device 120, for example, by detecting one or more wireless signals transmitted by the wearable oral device 120 (e.g., signals transmitted via a BLUETOOTH link or any other suitable wireless communication link). The user application 111 may present media content to the first user using the wearable oral device 120 and/or the user device. For example, the user application 111 may cause audio content to be presented to the user via the bone conduction component of the wearable oral device (e.g., by transmitting instructions for presenting the audio content via the bone conduction component). The user application 111 may also present, on a display of the user phone, media content, such as video content related to the audio content on the display, one or more user interfaces for controlling the playback of the audio content via the bone conduction component of the wearable oral device, one or more user interfaces for presenting a list of content items that may be consumed, shared, viewed, etc. by the user, etc.

As another example, the user application 111 may enable communications and/or interactions between the first user and/or one or more other users. More particularly, for example, the user application 111 may identify one or more other users that are related to the first user and may present content to facilitate communications between the first user and the identified one or more other users. In one implementation, the user application 111 may detect one or more nearby users (e.g., by determining that computing devices of the nearby users are within a predetermined proximity to the mobile phone of the first user). The user application may prompt the first user to interact with the nearby users (e.g., by playing audio content including the prompt via the bone conduction component of the wearable oral device, presenting one or more user interfaces on the display of the mobile device of the first user). In another implementation, the user application may facilitate the exchange of voice messages between the first user and a second user related to the first user (e.g., a social contact of the first user). For example, the user application may cause a voice message from the second user to be played via the wearable oral device (e.g., by sending data for playing the voice message via the bone conduction component to the wearable oral device). Examples of a social contact of the first user include a "friend," a "follower," a "subscriber," a "connection," a "contact," and/or any other user that is connected to the user via a content sharing platform, a social network platform, an email service, a phone service, and/or any other platform or service.

In some embodiments, the user application 111 may detect one or more user interactions with the wearable oral device 120 and perform one or more actions in view of the user interactions. For example, the user application 111 may detect that the wearable oral device 120 is positioned in a user's mouth (e.g., by receiving a signal indicating that the wearable oral device 120 is positioned in the user's mouth).

The user application 111 may unlock a screen of the user device 110, display certain content (e.g., a particular color, a blinking pattern), display health information of the user (e.g., a temperature of the user, information about the user's oral health, etc.).

As another example, the user application 111 may detect a user interaction by the first user with the wearable oral device 120 (e.g., a voice command or any other user input including a request for performing a search) and determine that the user interaction indicates a search query. The user application 111 may determine one or more search results based on the search query in view of the detected user interaction. For example, the user application 111 may send, to a server-side component 131 of the server 130, a request for performing a search based on the search query. The server-side component 131 may generate one or more search results and send a response including the search results to the user application 111. The user application 111 may then present media content including the search results to the first user using the wearable oral device 120 and/or the user device of the first user. For example, the user application 111 may send, to the wearable oral device 120, data for presenting audio content including the search results (e.g., a voice messaging describing the search results). The wearable oral device 120 may present the audio content using the bone conduction component.

As still another example, the user application 111 may detect a user interaction by the first user with the wearable oral device 120 and may determine that the user interaction indicates one or more actions to be performed by the user device, such as making a call, sharing a content item, sending a message, controlling playback of the audio content being played by the wearable oral device, making a payment, scheduling an event, requesting ride-sharing services, presenting a content item, etc. The user application 111 may then perform the actions and/or may cause one or more other applications running on the user device to perform the actions (e.g., by sending instructions to the applications).

In some embodiments, the user application 111 may perform one or more operations as described in connection with FIGS. 4, 5, and 6 below. The server-side component 131 may perform the operations described in connection with FIG. 6.

Figure 2:
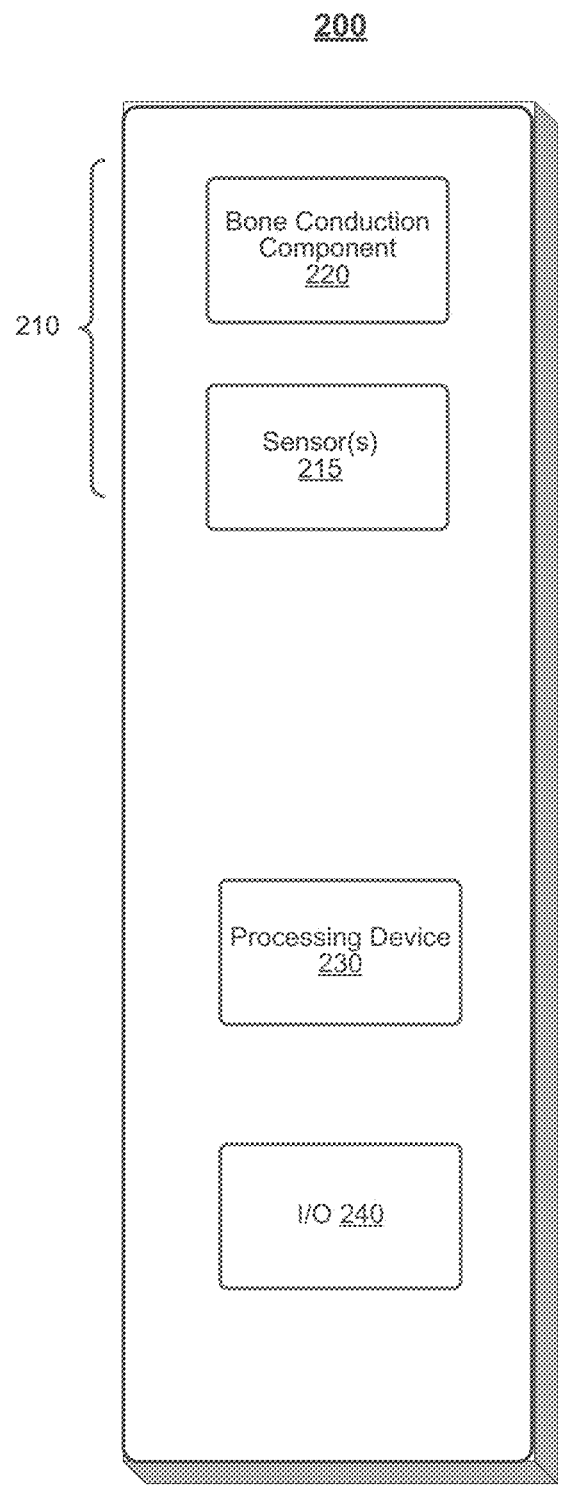
FIG. 2 is a block diagram illustrating a wearable oral device in accordance with some implementations of the disclosure.

FIG. 2 is a block diagram showing an example 200 of a wearable oral device in accordance with some embodiments of the present disclosure. As shown, wearable oral device 200 may include a mouthpiece 210, one or more sensors 215, a bone-conduction component 220, a processing device 230, and one or more input/output (I/O) devices 240.

The mouthpiece 210 may be positioned in a user's oral cavity. The mouthpiece 210 may be of any suitable size, shape, material, etc. for implementing various embodiments of the present disclosure. In some embodiments, one or more portions of the mouthpiece 210 may be covered by one or more edible materials (e.g., candy, ice cream, chocolate, etc.). In one implementation, the edible materials may be personalized for a particular user.

In some embodiments, the wearable oral device 200 may also include one or more sensors 215. The sensors may collect, analyze, etc. physiological data of a user of the wearable oral device 200. The physiological data may be collected by analyzing oral fluids of the user (e.g., a salvia sample), cells, microorganisms, etc. The physiological data may include data and/or information of one or more physiological parameters, such as a temperature, a glucose level, a type and/or a number of bacteria, volatile sulfur compounds, etc. In some embodiments, the sensor(s) 215 may also generate and/or output one or more signals indicating the physiological data. For example, the sensor(s) may output a first signal indicative of a value of a physiological parameter of the user (e.g., a temperature). As another example, the sensor(s) may output a second signal indicative of the values of a physiological parameter during a period of time. In some embodiments, the sensor(s) 215 may include one or more pressure sensors that can measure the pressure applied to the mouthpiece 210. The pressure sensors may further generate a signal indicative of the pressure applied to the mouthpiece 210. The signals generated by the sensor 215 may be transmitted to the processing device 230 for processing.

The sensors 215 may be placed in any suitable position to perform functions as described herein. For example, one or more of the sensors 215 may be placed in a chamber of the mouthpiece 210. As another example, one or more of the sensors 215 may be positioned on the mouthpiece. The sensors 215 may be communicatively coupled to the wearable oral device 200 and/or the other components of the wearable oral device 200.

The bone conduction component 220 may enable transmission of sound via bone conduction. For example, the bone conduction component 220 may convert audio data into vibrations that can be received directly by the cochlea of a user. In some embodiments, the bone-conduction component 220 may include a transducer. The audio content played via the bone conduction component 220 may be inaudible or approximately inaudible to outsiders. In some embodiments, the bone conduction component 220 may be located in the mouthpiece 210. For example, the mouthpiece 210 may include a chamber and the bone conduction component 220 may be positioned in the chamber.

The processing device 230 may include one or more processors (e.g., a microprocessor, digital signal processor, a controller, etc.), memory, communication interfaces, and/or any other suitable hardware components. The processing device 230 may also include one or more communication components that may communicate with another computing device according to one or more communication protocols, such as BLUETOOTH, NFC, WIFI, GSM, GPRS, UMTS, HSDPA, CDMA, etc. For example, the communication component(s) may generate and/or transmit wireless signals (e.g., BLUETOOTH signals) at certain intervals so that the presence of the wearable oral device and/or the processing device 230 may be detected by another device. In some embodiments, the communication component(s) may implement BLUETOOTH Low Energy (BLE) protocols. The communication components may include any suitable hardware, software, firmware, the like, or a combination thereof.

The I/O device(s) 240 may include one or more devices that may enable a user to interact with the wearable oral device 200 and/or to provide user inputs. For example, the I/O device(s) 240 may include a microphone or any other suitable device that can receive audio input (e.g., one or more voice commands issued by a user). As another example, the I/O device(s) 240 may include a touchscreen, keypad, touchpad, etc. that can receive text input, gestures, etc. As still another example, the I/O device(s) 240 may include one or more buttons (e.g., an on/off button or switch, one or more buttons for adjusting volumes of audio content, etc.).

The I/O device(s) 240 may include output devices, such as a display, a speaker, etc. In some embodiments, the I/O device(s) 240 may include one or more light-emitting diodes (LEDs) and/or any other light-emitting devices that can emit light.

In some embodiments, the I/O device(s) 240 may include a touchscreen. The touchscreen may receive user inputs for controlling the playback of media content via the wearable oral device 200 (e.g., gestures and other user input for selecting, playing, rewinding, forwarding, sharing, etc. a content item). The touchscreen may also present media content (e.g., displaying video content, images, user interfaces, etc.).

The processing device 230 may detect one or more user interactions by a user with the wearable oral device 200. As an example, the processing device 230 may detect that the user interacts with the wearable oral device 200 by detecting that one or more portions of the wearable oral device 200 (e.g., the mouthpiece 210) are positioned in the oral cavity of the user. More particularly, for example, the processing device 230 may receive, from one or more sensors 215, a signal indicating a temperature of the user and/or a pressure applied to the mouthpiece 210 by the user. The processing device 230 may analyze the signal and may determine that the wearable oral device 200 is positioned in the oral cavity of the user in response to detecting a predetermined temperature or pressure based on the signal.

As another example, the processing device 230 may detect the user interactions by detecting one or more user inputs provided by the user via the I/O device(s) 240 (e.g., one or more voice commands, gestures, text inputs, etc.).

In some embodiments, the processing device 230 may generate a signal indicative of the detected user interactions. The signal indicative of the detected user interactions may include information indicative of the detection of the user interactions (e.g., a Boolean value indicating whether a user interaction by the first user with the wearable oral device is detected), one or more user inputs related to the user interactions (e.g., one or more voice commands, text input, gestures, etc.), and/or any other suitable information and/or data related to the one or more user interactions.

The processing device 230 may transmit the signal indicative of the detected user interactions to a computing device, such as a mobile phone or any other computing device of the user that is interacting with the wearable oral device 200. In some embodiments, the signal indicative of the detected user interactions may be transmitted via one or more suitable communication links between the wearable oral device 200 and the computing device, such as network links, wireless links (e.g., BLUETOOTH links, Wi-Fi links, etc.), hardwired links, any other suitable communication links, or a combination of such links.

The processing device 230 may further receive data for presenting media content from the computing device and may present the media content accordingly. The data for presenting the media content may include instructions for presenting one or more content items (e.g., an instruction for presenting audio content via the bone conduction component 220, an instruction for presenting media content on a display of the wearable display device), the media content to be presented (e.g., audio content, video content), etc. In some embodiments, the processing device 230 may perform one or more operations as described in connection with FIG. 3 below.

While certain components of the wearable oral device are illustrated in FIG. 2, this is merely illustrative. The wearable oral device may include a battery (e.g., a rechargeable battery), a display, wires, and/or any other suitable component for implementing the wearable oral device in accordance with various embodiments of the present disclosure. For example, the wearable oral device may include memory or any other suitable storage device that stores media content. The processing device 230 may present the media content to a user when the user interacts with the wearable oral device 200 (e.g., by placing the wearable oral device 200 in the user's mouth, by providing user inputs, etc.). In some embodiments, the wearable oral device 200 may be a vaporizer (e.g., an electronic cigarette) and may include a cartridge, a heating element, etc.

Figure 3A:
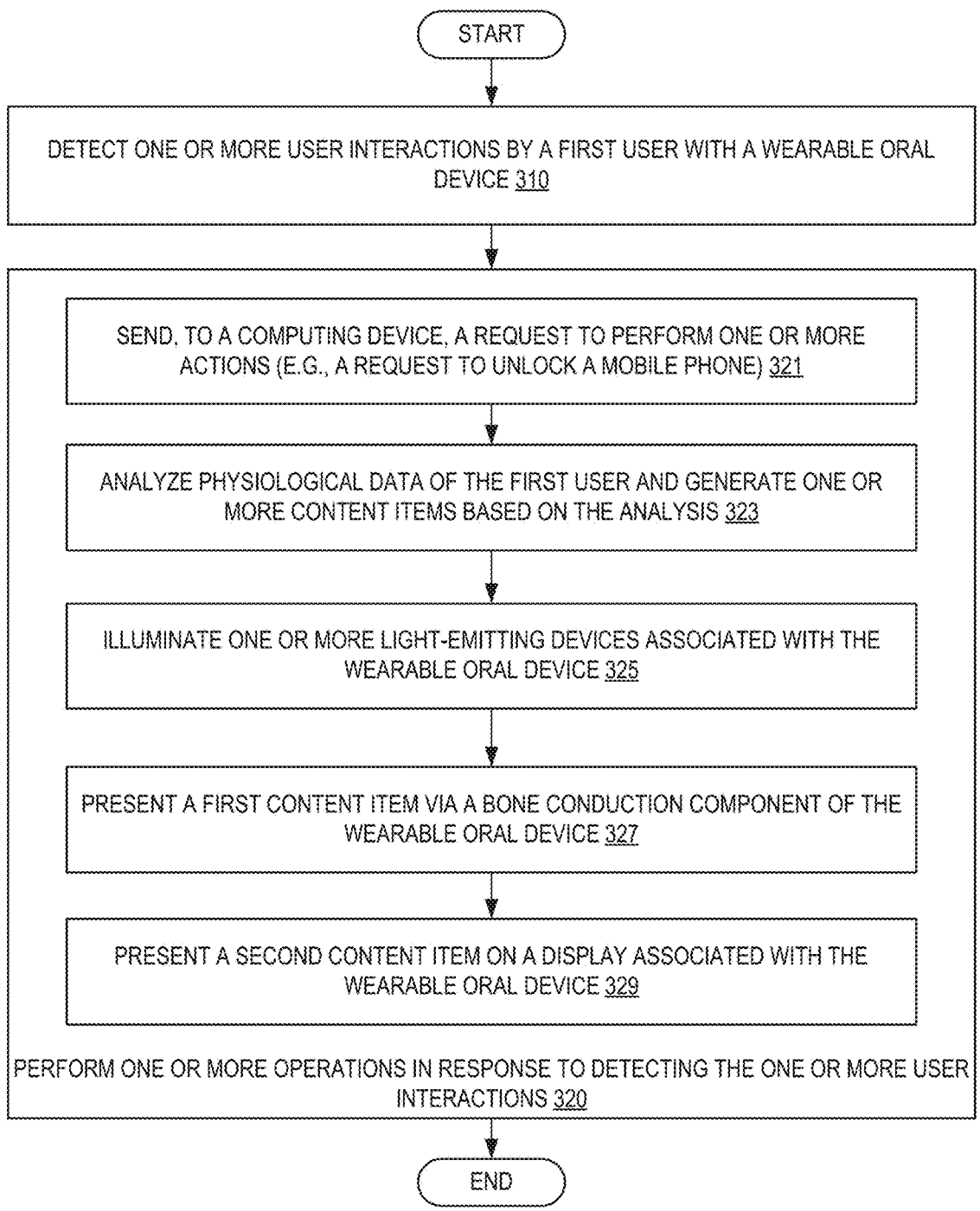
FIGS. 3A and 3B are flow diagrams illustrating methods for implementing a wearable oral device according to some implementations of the disclosure.
Figure 3B:
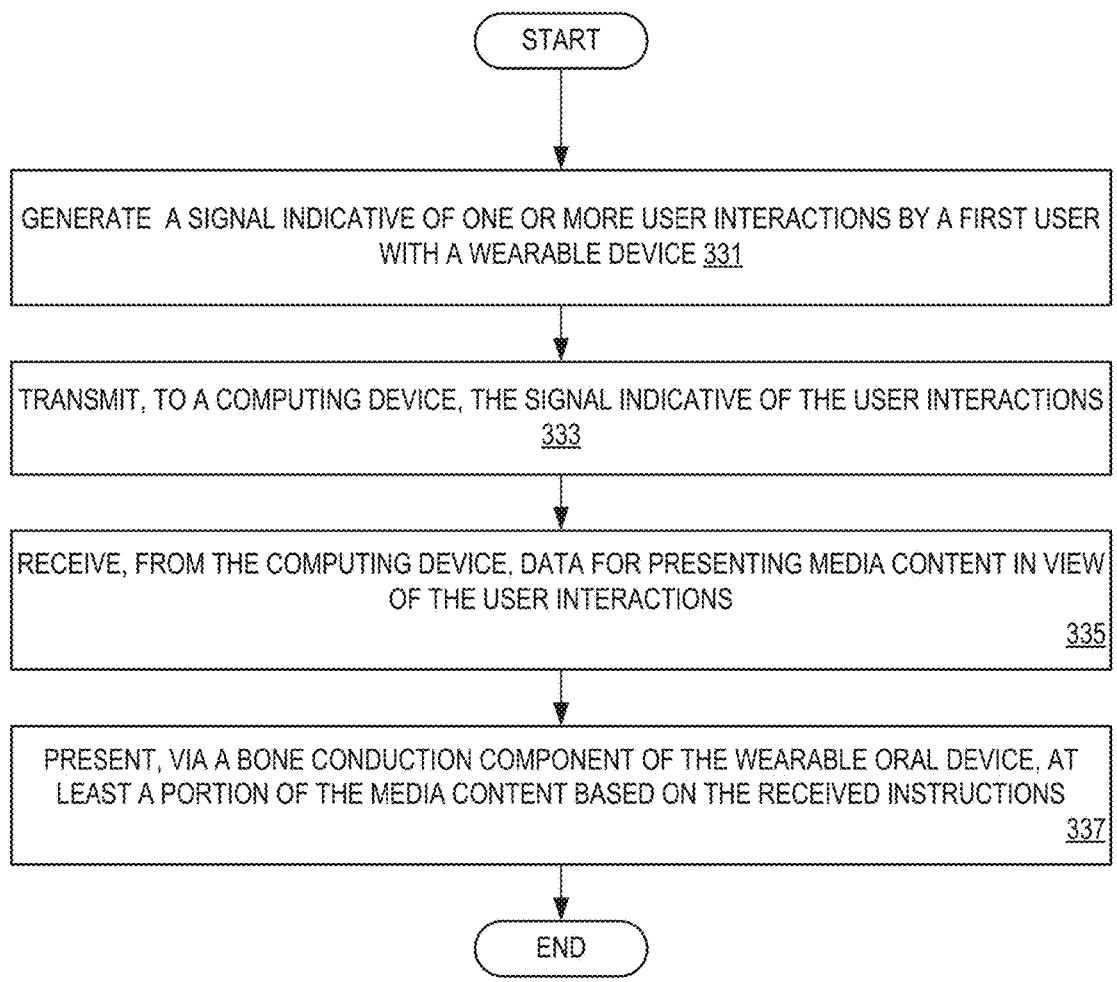

FIGS. 3A and 3B are flow diagrams illustrating methods 300 and 330 for implementing a wearable oral device according to some implementations of the disclosure. The methods 300 and 330 may be performed by processing logic that comprises hardware (e.g., circuitry, dedicated logic, programmable logic, microcode, etc.), software (e.g., instructions run on a processing device to perform hardware simulation), or a combination thereof.

Method 300 may begin at block 310 when the processing device detects one or more user interactions by a first user with a wearable oral device. Detecting the user interactions may involve detecting that the first user is interacting with one or more portions of the wearable oral device in any suitable manner. For example, the processing device may detect a first user interaction by detecting that a mouthpiece of the wearable oral device is placed in the mouth of the first user. As another example, the processing device may detect a second user interaction by detecting a user input provided by the first user via one or more portions of the wearable oral device (e.g., an input device, such as a microphone, keypad, touchscreen, etc.). The user input may include, for example, one or more voice commands, text input, gestures, etc. In some embodiments, the user interactions and/or the user input may correspond to a user request for performing one or more actions by the wearable oral device and/or any other suitable device. For example, the user interactions and/or the user input may include a user request for performing a search, a user request for sharing content, a user request for making a call, etc.

At block 320, the processing device may perform one or more operations in response to detecting the one or more user interactions. The operations may be performed in view of the user interactions by performing one or more operations depicted in blocks 321-337.

At block 321, the processing device can send, to a computing device, a request to perform one or more actions. For example, the request may include a request to unlock a user device (e.g., a mobile phone) of the first user, a request to light up a screen of the user device, etc. As such, the processing device can cause the user device to be unlocked in response to detecting that the first user is interacting with the wearable oral device.

At block 323, the processing device can analyze physiological data of the first user and can generate one or more content items based on the analysis. The physiological data may include data and/or information of one or more physiological parameters, such as a temperature, a glucose level, a type and/or a number of bacteria, volatile sulfur compounds, etc. The processing device may analyze the physiological data to generate a report of the first user's oral health, to determine whether a physiological parameter (e.g., an oral temperature) of the first user is greater than a predetermined threshold, etc. The content items may include, for example, a notification indicating that the physiological parameter is greater than the threshold (e.g., the first user having a fever), the report of the first user's oral health, etc.

At block 325, the processing device can illuminate one or more light-emitting devices associated with the wearable oral device. In some embodiments, the processing device may illuminate the light-emitting devices in response to detecting one or more other wearable oral devices in a predetermined proximity to the wearable oral device.

At block 327, the processing device can present a first content item via a bone conduction component of the wearable oral device. The first content item may include any suitable audio content. As an example, the first content item may include audio content related to the first user, such as audio content provided by the first user (e.g., audio content uploaded by the first user using a user device, audio content identified by the first user using the wearable oral device and/or any other user device), audio content stored on the wearable oral device, audio content stored on a storage device associated with the first user, audio content that the first user has interacted with, etc.).

As an example, the first content item may include audio content related to physiological data of the first user. As another example, the first content item may include audio content related to a point of interest. As a further example, the first content item may include audio content stored on a storage device associated with the wearable oral device.

In some embodiments, the processing device may present the first content item in response to determining that the wearable oral device is in a predetermined proximity to the point of interest. The first content item may include information about the point of interest (e.g., an introduction to the point of interest, a message prompting the first user to interact with the point of interest, etc.).

In some embodiments, the first content item may include content items (e.g., audio content) generated based on one or more user interaction with the wearable oral device by the first user detected by the processing device. For example, the processing device may detect a first user interaction with the wearable oral device by the first user. The first user interaction may correspond to placement of the mouthpiece of the wearable oral device in the first user's mouth. In response to detecting the first user interaction, the processing device may automatically present media content related to the first user (e.g., audio content predefined by the first user, audio content stored on the wearable oral device, etc.), media content of one or more other users related to the first user (e.g., information of one or more nearby users, a voice message sent to the first user by a second user, etc.), media content related to one or more points of interest near the first user, etc. In some embodiments, the first content item may be provided by a computing device associated with the first user. For example, the first content item may be presented by performing one or more operations depicted in blocks 331-337.

In some embodiments, at block 329, the processing device can present a second content item on a display associated with the wearable oral device. The second content item may include video content related to the physiological data of the first user, video content related to a point of interest, video content stored in the storage device associated with the wearable oral device, video content provided by the computing device associated with the first user, etc.

Method 330 may begin at block 331, where the processing device may generate a signal indicative of one or more user interactions by the first user with the wearable oral device. The one or more user interactions may be detected as described in connection with block 310 above. The signal indicative of the detected one or more user interactions may include any suitable information and/or data related to the one or more user interactions. For example, the signal may include information indicative of the detection of the user interactions (e.g., a Boolean value indicating whether a user interaction by the first user with the wearable oral device is detected). As another example, the signal may include one or more user inputs related to the user interactions (e.g., one or more voice commands, text input, gestures, etc.).

At block 333, the processing device can transmit the signal indicative of the user interactions to a computing device. In some embodiments, the computing device may be associated with the first user. For example, the computing device may include a mobile device (e.g., a mobile phone, tablet computer, watch) of the first user. In some embodiments, the processing device may transmit the signal indicative of the user interactions to the computing device via any suitable wireless communication protocol.

At block 335, the processing device may receive, from the computing device, data for presenting media content generated in view of one or more user interactions. The media content may be generated in view of the user interactions and may include audio content, video content, images, graphics, and/or any other suitable content. The data for presenting the media content may include any suitable information for providing playback of the media content. For example, the data for presenting the media content may include one or more instructions for presenting the media content (e.g., one or more instructions for playing audio content via a bone conduction component of the wearable oral device). As another example, the data for presenting the media content may include the media content (e.g., the audio content to be played via the bone conductor component of the wearable oral device).

In some embodiments, the media content in view of the user interactions may include one or more content items related to the first user, such as media content recorded for the first user, media content with which the first user has interacted (e.g., media content consumed, liked, shared, etc. by the first user via a social account of the first user), etc.

In some embodiments, the media content in view of the user interactions may include one or more content items related to one or more other users. The one or more other users may include another user related to the first user, such as a social contact of the first user, one or more other users that share a common interest with the first user, one or more other users that are in a predetermined proximity to the first user, etc.

In some embodiments, the media content in view of the user interactions may include content generated in response to a user request corresponding to the user interactions. In some embodiments in which the user interactions by the first user with the wearable oral device may correspond to a search query (e.g., a request for searching for nearby places), the media content in view of the user interactions may include content presenting search results generated in response to the user request for performing the search.

At block 337, the processing device may present, via a bone conduction component of the wearable oral device, at least a portion of the media content based on the received instructions. For example, upon receiving data for presenting audio content via the bone conduction component of the wearable oral device, the processing device can cause the audio content to be played via the bone conduction component. In some embodiments, the audio content played via the bone conduction component may include a voice message from a second user (e.g., a user related to the first user), a voice message prompting the first user to interact with the second user, and/or any other content related to one or more other users related to the first user. In some embodiments, the audio content played via the bone conduction component may include audio data stored in a storage device associated with the wearable oral device or other audio data related to the first user.

As another example, upon receiving data for presenting video content, images, etc. on a display of the wearable oral device, the processing device can cause the video content, images, etc. to be played on the display of the wearable oral device.

Figure 4:
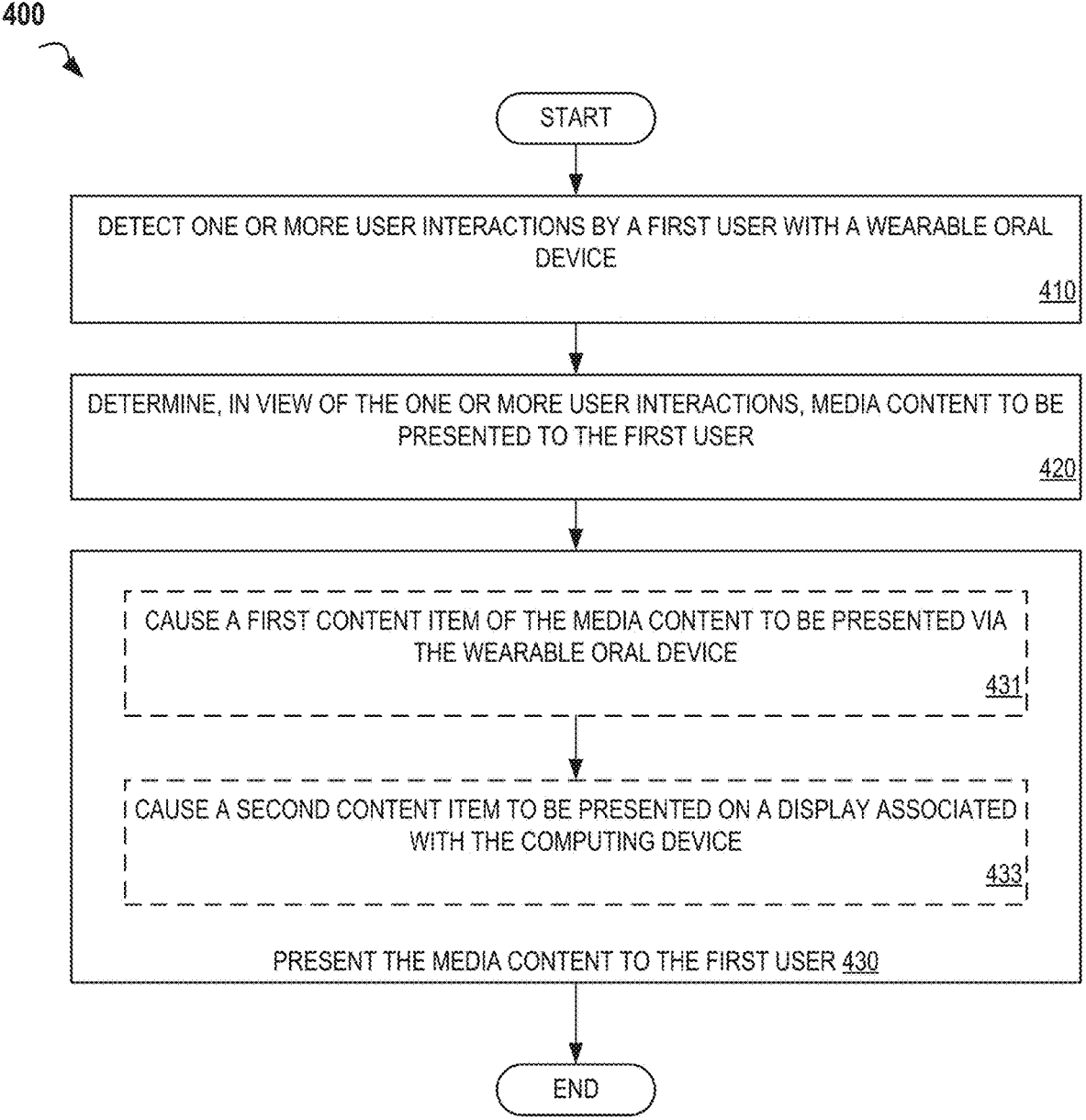
FIG. 4 is a flow diagram illustrating a method for performing actions in view of user interactions with a wearable oral device according to some implementations of the disclosure.

FIG. 4 is a flow diagram illustrating a method 400 for performing actions in view of user interactions with a wearable oral device according to some implementations of the disclosure. The method 400 may be performed by processing logic that comprises hardware (e.g., circuitry, dedicated logic, programmable logic, microcode, etc.), software (e.g., instructions run on a processing device to perform hardware simulation), or a combination thereof.

Method 400 may begin at block 410 when a processing device detects one or more user interactions by a first user with a wearable oral device. For example, the processing device may detect the one or more user interactions by receiving, from the wearable oral device, a signal indicative of the one or more user interactions (e.g., the signal described in connection with blocks 320 and 332 of FIG. 3).

At block 420, the processing device may determine, in view of the one or more user interactions, media content to be presented to the first user. The media content may be and/or include any suitable content, such as audio content, video content, images, graphics, etc.

In one implementation, the media content to be presented to the first user may include one or more content items associated with the first user. For example, the content items related to the first user may include one or more content items stored in a storage device associated with the wearable oral device (e.g., a local storage of the wearable oral device, a cloud-based storage connected to the wearable oral device, etc.). As another example, the content items related to the first user may include one or more content items with which the first user has been interacted (e.g., consumed, liked, shared, etc. on a content sharing platform). As a further example, the content items related to the first user may include one or more content items stored in a storage device associated with the processing device.

In another implementation, the media content to be presented to the first user may include one or more content items related to one or more other users related to the first user, such as a social contact of the first user, one or more other users that share a common interest with the first user, one or more other users that are in a predetermined proximity to the first user, etc. For example, the media content to be presented to the first user may include a voice message from a second user that is related to the first user. As another example, the media content related to the one or more other users may include content items that prompt the first user to interact with the one or more other users via a user application (e.g., to exchange messages with the other user, to share content with the other users).

In another implementation, the media content in view of the user interactions may include content generated in response to a user request corresponding to the user interactions. In some embodiments in which the user interactions by the first user with the wearable oral device may correspond to a user request for performing a search (e.g., a search for nearby places), the media content in view of the user interactions may include content presenting search results generated in response to the user request.

To determine the media content to be presented to the first user, the processing device may identify the user interactions by the first user with the wearable oral device (e.g., by processing the signal indicative of the user interactions by the first user with the wearable oral device). The processing device may also perform one or more actions based on the identified user interactions, such as performing a search for a search query provided in the user interactions (e.g., by sending a search request to a server), retrieving and/or generating media content identified by the user interactions, transmitting information related to the user interactions to a server for processing, running one or more applications on a computing device of the first user, etc. Alternatively or additionally, the processing device can transmit, to a server, a request for media content related to the user interactions. The processing can then determine the content to be presented to the first user based on a response received from the server.

In some embodiments, the processing device may determine the media content by performing one or more operations as described in connection with FIG. 6 below.

At block 430, the processing device can present the media content to the first user. For example, at block 431, the processing device can cause a first content item of the media content to be presented via the wearable oral device. The first content item may include audio content. More particularly, for example, the processing device can transmit, to the wearable oral device, data for presenting the first content item via a bone conduction component of the wearable oral device. In one implementation, the data for presenting the first content item include the audio content to be played via the bone conduction component of the wearable oral device. In another implementation, the data for presenting the first content item does not include the audio content to be played via the bone conduction component. In such implementation, the audio content may be stored on a storage device associated with the wearable oral device, such as a local storage device of the wearable oral device, a cloud storage associated with the wearable oral device, etc.

As another example, at block 433, the processing device can cause a second content item to be presented on a display associated with the computing device. For example, the second content item may include a user interface for controlling the playback of the first content item. As another example, the second content item may include video content associated with the audio content. As yet another example, the second content item may include a user interface for presenting a list of content items related to the first user and/or one or more other users related to the first user and providing playback of the content items.

Figure 5:
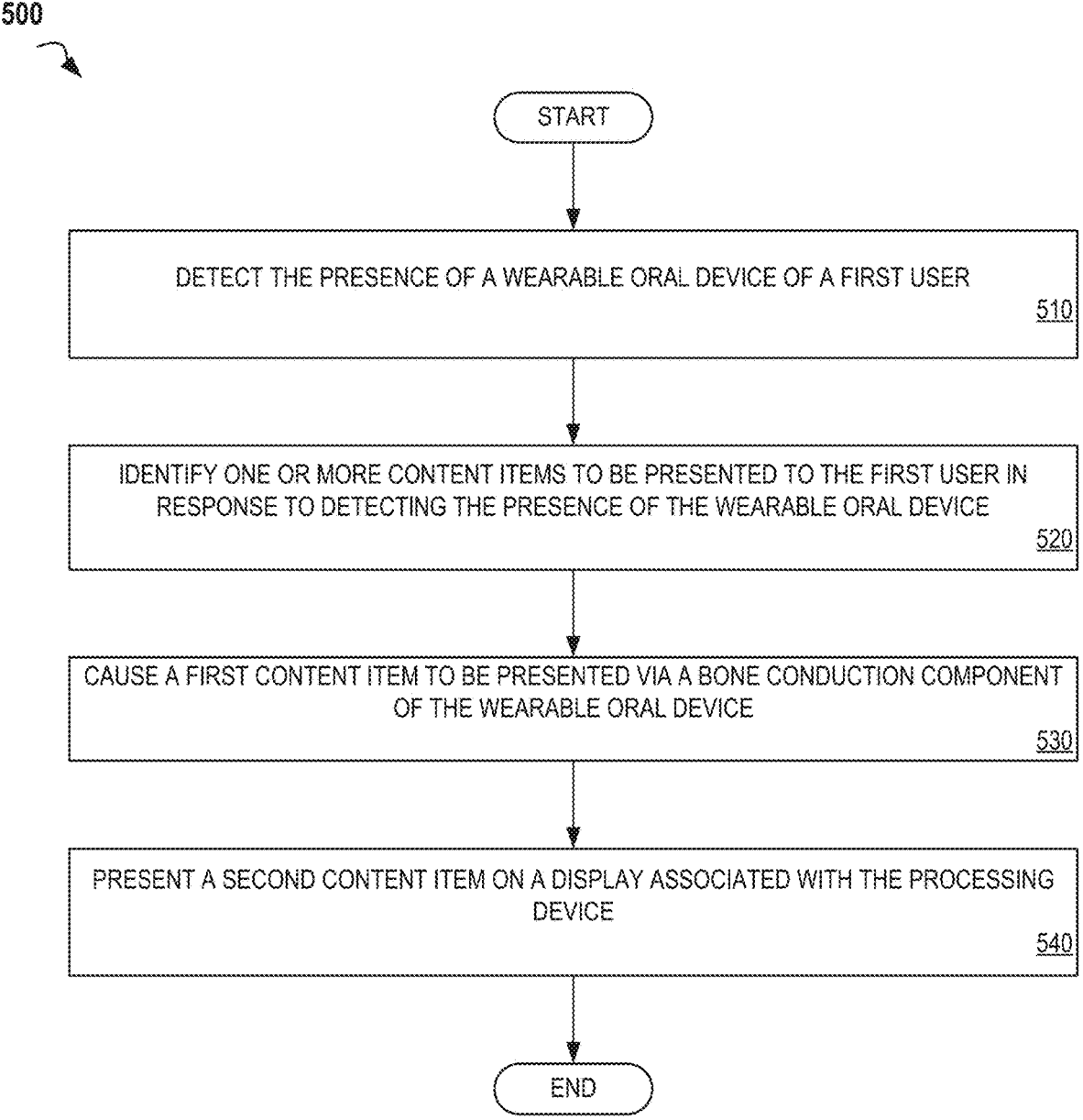
FIG. 5 is a flow diagram illustrating a method for presenting media content for a user of a wearable oral device according to some implementations of the disclosure.

FIG. 5 is a flow diagram illustrating a method 500 for presenting media content for a user of a wearable oral device according to some implementations of the disclosure. The method 500 may be performed by processing logic that comprises hardware (e.g., circuitry, dedicated logic, programmable logic, microcode, etc.), software (e.g., instructions run on a processing device to perform hardware simulation), or a combination thereof.

Method 500 begins at block 510 when the processing device detects the presence of a wearable oral device of a first user. For example, the processing device can detect the presence of the wearable oral device by detecting one or more communication signals transmitted by the wearable oral device (e.g., transmitting communication signals containing identification information at regular intervals using a wireless technology and/or protocol, such as BLUETOOTH, NFC, WIFI, GSM, GPRS, UMTS, HSDPA, CDMA, etc. In some embodiments, the processing device can detect the presence of the wearable oral device in response to receiving a signal indicative of one or more user interactions with the wearable oral device.

At block 520, the processing device can identify one or more content items to be presented to the first user in response to detecting the presence of the wearable oral device. For example, the processing device can identify one or more content items related to the first user. As another example, the processing device can identify one or more content items related to one or more other users related to the first user. In some embodiments, the processing device may determine the media content by performing one or more operations as described in connection with FIG. 6 below. In some embodiments, the processing device may send, to the first user to a server, a request for the content items to be presented. The processing device may then identify the content items to be presented to the first user based on a response provided by the server in response to the request.

At block 530, the processing device can cause a first content item to be presented via a bone conduction component of the wearable oral device. The first content item may comprise audio content. To cause the first content item to be presented via the bone conduction component, the processing device may transmit data for providing playback of the first content item (e.g., one or more instructions for playing the first content item, the audio content). In one implementation, the first content item may be a content item stored in a storage device associated with the wearable oral device. In another implementation, the first content item may be a content item related to the first user (e.g., a content item with which the first user has interacted). In some embodiments, the first content item may be a content item related to a second user (e.g., a voice message from the second user, a voice message prompting the first user to interact with the second user).

At block 540, the processing device can present a second content item on a display associated with the processing device. The second content item may include any suitable content. As an example, the second content item may include a user interface for controlling playback of the first content item. The user interface may include one or more elements ("UI" elements) for playing the first content item, pausing the playback of the first content item, rewinding or fast-forwarding the playback of the first content item, selecting a next content item to be played, etc. As another example, the second content item may include a user interface for presenting a list of content items related to the first user (e.g., one or more of the content items identified at block 620). The user interface may also include one or more UI elements that may enable a user to request playback, sharing, etc. of one or more of the content items in the list. As a further example, the second content item may include a video related to the first content item (e.g., the video content corresponding to the audio content contained in the first content item).

Figure 6:
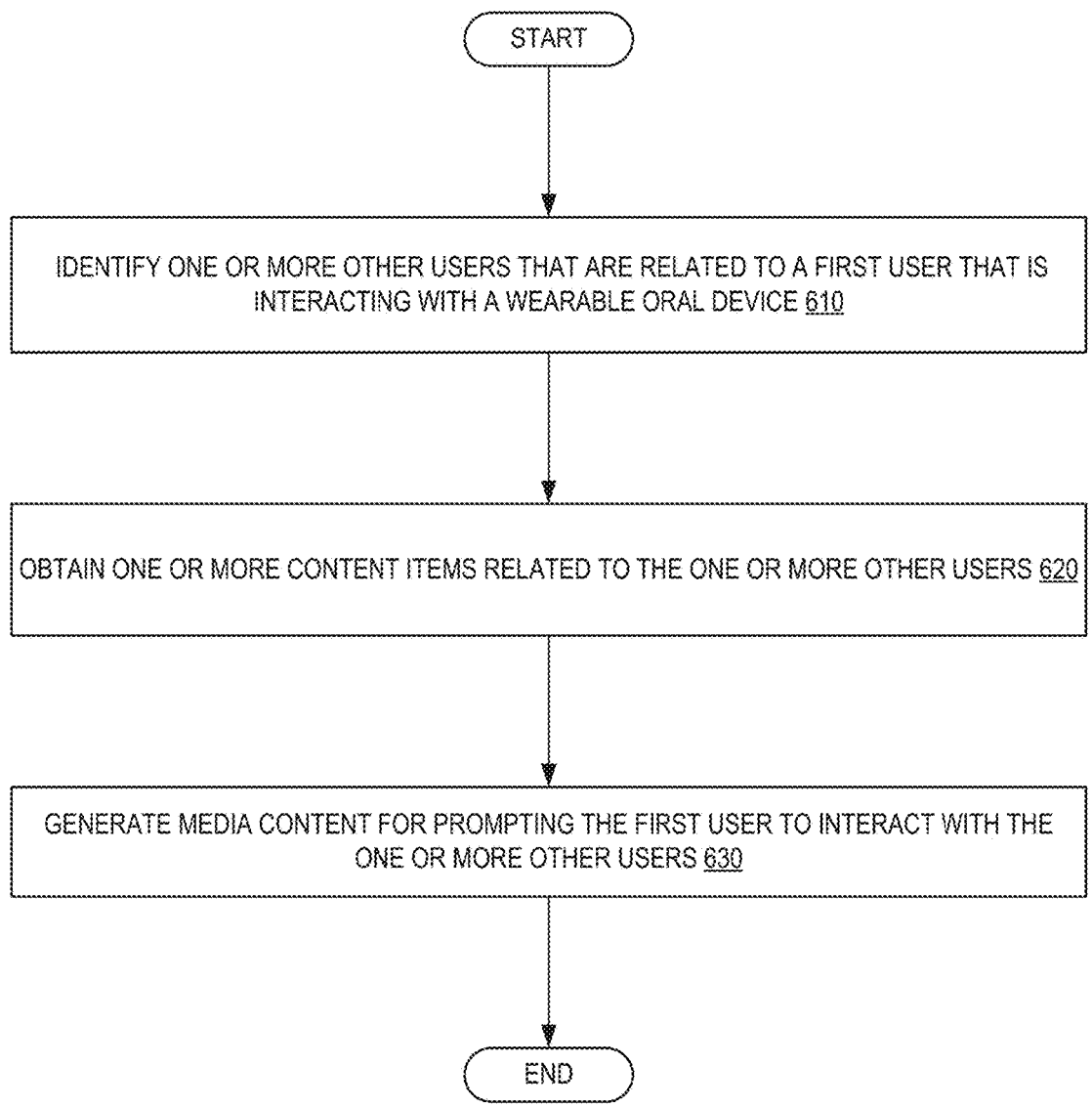
FIG. 6 is a flow diagram illustrating a method for determining media content to be presented to a first user of a wearable oral device according to some implementations of the disclosure.

FIG. 6 is a flow diagram illustrating a method 600 for determining media content to be presented to a first user according to some implementations of the disclosure. The method 600 may be performed by processing logic that comprises hardware (e.g., circuitry, dedicated logic, programmable logic, microcode, etc.), software (e.g., instructions run on a processing device to perform hardware simulation), or a combination thereof.

Method 600 may begin at block 610 when the processing device identifies one or more other users (e.g., a second user, a third user, a group of users, etc.) that are related to a first user that is interacting with a wearable oral device. For example, the processing device can determine that a second user is related to the first user in response to determining that the second user is a social contact of the first user. Examples of a social contact of the first user include a "friend," a "follower," a "subscriber," a "connection," a "contact," and/or any other user that is connected to the user via a content sharing platform, a social network platform, an email service, a phone service, and/or any other platform or service.

As another example, the processing device can determine that a third user is related to the first user in response to determining that the first user and the third user share one or more common interests. In some embodiments, the processing device may identify the common interests in view of public data in user profiles of the first user and the third user on a social network. In some embodiments, the processing device may identify the common interests based on one or more user inputs provided by the first user and/or the third user.

As a further example, the processing device can determine that a fourth user is related to the first user in response to determining that a user device of the first user (also referred to as the "first user device") and a user of the fourth device (also referred to as the "second user device") are within a predetermined proximity. In some embodiments, the processing device can identify the fourth user by determining that the first user device and the second device are in a particular wireless network and/or connected to a particular device (e.g., a network router). In some embodiments, the processing device can identify the fourth user by determining that the position of the first user device and the position of the second user device are within the predetermined proximity based on positioning information of the first user device and the second user device. In some embodiments, the processing device can identify a plurality of users as nearby users of the first user in response to determining that the plurality of users and the first user are within the predetermined proximity.

At block 620, the processing device can obtain one or more content items related to the one or more other users. For example, the processing device can obtain one or more content items with which the one or more other users have interacted (e.g., consumed, liked, shared, etc.). As another example, the processing device can obtain one or more content items from the one or more other users (e.g., by receiving the content items from a computing device of the one or more other users, a server, or any other suitable device). More particularly, for example, the processing device can obtain a voice message from a second user and/or a content item shared by the second user to facilitate communication between the first user and the second user.

At block 630, the processing device can generate media content for prompting the first user to interact with the one or more other users. For example, the processing device can generate one or more user interfaces, voice messages, and/or any other suitable content for informing the first user of one or more nearby users and prompting the first user to send a message to the nearby users or interact with the nearby users in any other suitable manner.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term "article of manufacture," as used herein, is intended to encompass a computer program accessible from any computer-readable device or storage media.

Figure 7:
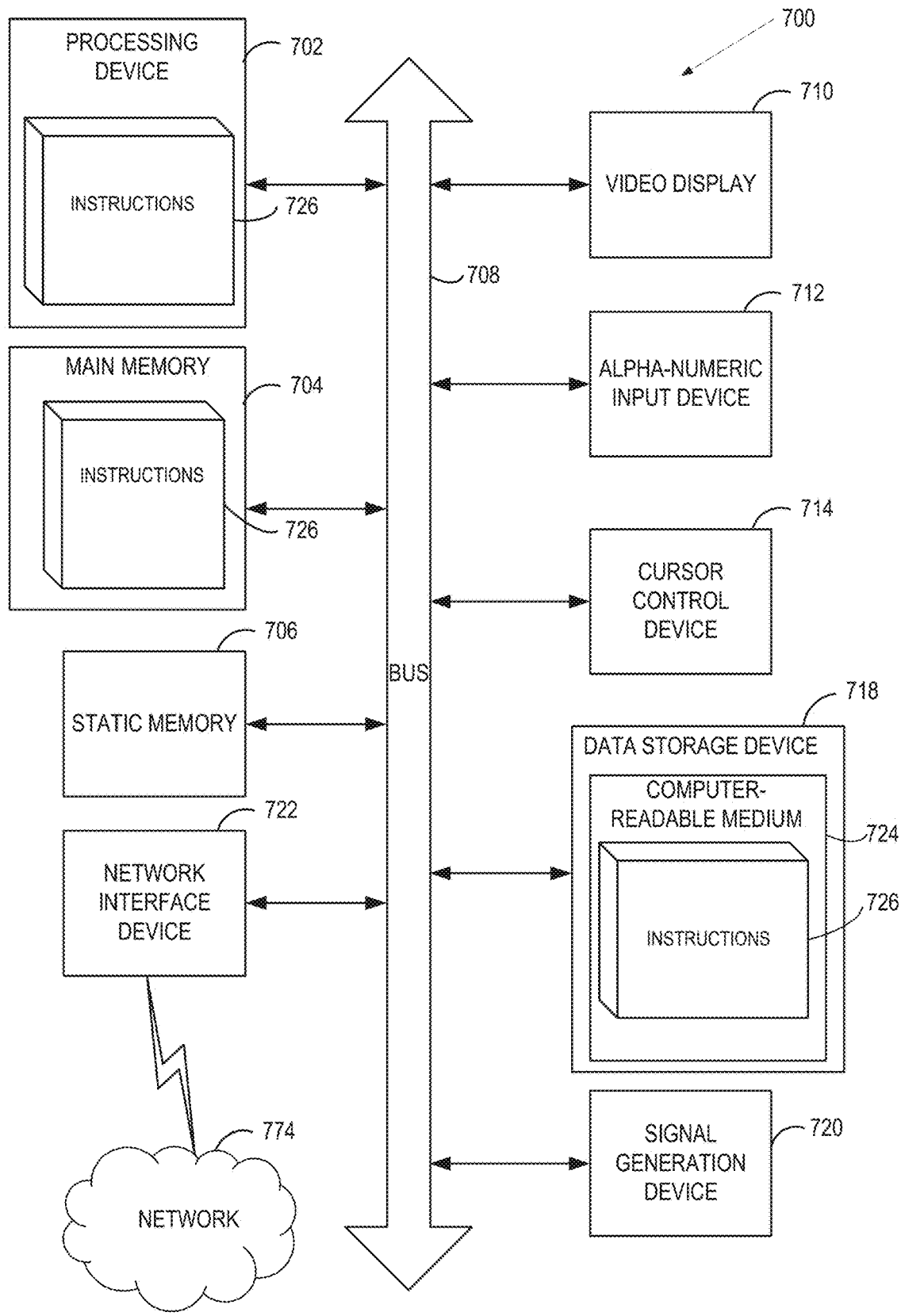
FIG. 7 is a block diagram illustrating an example of a computer device according to some implementations of the present disclosure.

FIG. 7 illustrates a diagrammatic representation of a machine in the exemplary form of a computer device 700 within which a set of instructions, for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 700 includes a processing device (processor) 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 1218, which communicate with each other via a bus 708.

Processing device 702 represents one or more general-purpose processing devices such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 702 may also be one or more special-purpose processing devices such as an application specific integrated circuit (ASIC), a field programmable gate array (FPGA), a digital signal processor (DSP), network processor, or the like. The processing device 702 is configured to execute instructions 726 for performing the operations and steps discussed herein.

The computer system 700 may further include a network interface device 722. The computer system 700 also may include a video display unit 710 (e.g., a liquid crystal display (LCD), a cathode ray tube (CRT), or a touch screen), an alphanumeric input device 712 (e.g., a keyboard), a cursor control device 714 (e.g., a mouse), and a signal generation device 720 (e.g., a speaker).

The data storage device 718 may include a computer-readable storage medium 724 on which is stored one or more sets of instructions 726 (e.g., software) embodying any one or more of the methodologies or functions described herein. The instructions 726 may also reside, completely or at least partially, within the main memory 704 and/or within the processor 702 during execution thereof by the computer system 700, the main memory 704 and the processor 702 also constituting computer-readable storage media. The instructions 726 may further be transmitted or received over a network 774 via the network interface device 722.

In one embodiment, the instructions 726 include instructions for implementing the user application 111 and/or the server-side component 131 described with respect to FIG. 1, and/or a software library containing the methods described in the present disclosure (e.g., the methods 300, 400, 500, and 600 of FIGS. 3-6). While the computer-readable storage medium 724 is shown in an exemplary implementation to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "detecting", "determining", "enabling", "identifying," "presenting," "searching," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may include a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A wearable oral device, comprising:
a mouthpiece;
a bone conduction component; and
a processing device to:
   detect one or more user interactions by a first user with the wearable oral device, wherein the one or more user interactions comprise a first user interaction by the first user with the mouthpiece; and
   perform one or more operations in response to detecting the one or more user interactions, wherein the one or more operations comprise:
      presenting a first content item via the bone conduction component of the wearable oral device, wherein the first content item comprises audio content related to one or more of: the first user, physiological data of the first user, the point of interest; and
      sending, to a user device, a request for unlocking the user device, wherein the user device comprises a user application that causes the audio content to be presented to the first user via the bone conduction component, wherein the user application is programmed to access, retrieve, present, and navigate content served by a server, wherein the user application displays an embedded media player, wherein the user application detects the user interactions by the first user with the wearable oral device and determines that the user interactions indicate a search query, wherein the user application determines one or more search results based on the search query in view of the detected user interactions, wherein the user application sends a request for performing a search based on the search query to a server-side component of the server, wherein the server-side component generates the one or more search results and sends a response including the one or more search results to the user application;
   wherein the processing device is further to:
      in view of the detection of the first user interaction and a determination that the wearable oral device is in a predetermined proximity to the point of interest, present media content related to the point of interest;
   wherein the user application enables communications between the first user and one or more other users, wherein the user application identifies the one or more other users that are related to the first user and presents content to facilitate communications between the first user and the one or more other users;
   wherein the media content in view of the one or more user interactions by the first user with the wearable oral device comprises one or more content items related to a second user.

2. The wearable oral device of claim 1, wherein the one or more operations further comprise:
analyzing physiological data of the first user; and
generating the first content item in view of the physiological data.

3. The wearable oral device of claim 2, further comprising:
a sensor configured to collect the physiological data.

4. The wearable oral device of claim 1, wherein the one or more operations further comprise:
illuminating one or more light-emitting devices.

5. The wearable oral device of claim 4, wherein the processing device is further to illuminate the one or more light-emitting devices in response to detecting one or more other wearable oral devices.

6. The wearable oral device of claim 1, wherein the mouthpiece is coated with an edible material.

7. The wearable oral device of claim 1, wherein the wearable oral device comprises at least one of an electronic cigarette, a toothbrush, a pacifier, a bottle with straw, or an eating utensil.

8. The wearable oral device of claim 1, wherein the second user is at least one of a social contact of the first user, a user that is within a predetermined proximity to the first user, or a user that shares a common interest with the first user.

9. The wearable oral device of claim 8, wherein the media content comprises a voice message from the second user.

10. The wearable oral device of claim 1, wherein the one or more operations further comprise: transmitting, to a computing device associated with the first user, a signal indicative of the one or more user interactions by the first user with the wearable oral device.

11. The wearable oral device of claim 10, wherein the processing device is further to:
  receive, from the computing device, data for presenting media content, wherein the media content is generated in view of the one or more user interactions by the first user with the wearable oral device; and
  present, based on the received instructions, the first content item via the bone conduction component of the wearable oral device.

12. The wearable oral device of claim 1, the one or more operations further comprise:
  presenting a second content item on a display of the wearable oral device.

13. A method, comprising:
  detecting one or more user interactions by a first user with a wearable oral device, wherein the one or more user interactions comprise a first user interaction by the first user with a mouthpiece of the wearable oral device; and
  in response to detecting the one or more user interactions, performing one or more operations in view of the one or more user interactions, wherein the one or more operations comprise:
    presenting a first content item via the bone conduction component of the wearable oral device, wherein the first content item comprises audio content related to one or more of: the first user, physiological data of the first user, the point of interest;
    sending, to a user device, a request for unlocking the user device, wherein the user device comprises a user application that causes the audio content to be presented to the first user via the bone conduction component, wherein the user application is programmed to access, retrieve, present, and navigate content served by a server, wherein the user application displays an embedded media player, wherein the user application detects the user interactions by the first user with the wearable oral device and determines that the user interactions indicate a search query, wherein the user application determines one or more search results based on the search query in view of the detected user interactions, wherein the user application sends a request for performing a search based on the search query to a server-side component of the server, wherein the server-side component generates the one or more search results and sends a response including the one or more search results to the user application; and
    in view of the detection of the first user interaction and a determination that the wearable oral device is in a predetermined proximity to the point of interest, presenting media content related to the point of interest;
    wherein the user application enables communications between the first user and one or more other users, wherein the user application identifies the one or more other users that are related to the first user and presents content to facilitate communications between the first user and the one or more other users; and
    wherein the media content in view of the one or more user interactions by the first user with the wearable oral device comprises one or more content items related to a second user.

14. The method of claim 13, wherein the one or more operations further comprise:
  presenting a second content item on a display of the wearable oral device.

15. The method of claim 13, further comprising:
  transmitting, to a computing device associated with the first user, a signal indicative of the one or more user interactions by the first user with the wearable oral device;
  receiving, from the computing device, data for presenting media content in view of the one or more user interactions by the first user with the wearable oral device; and
  presenting, based on the received instructions, the first content item via the bone conduction component of the wearable oral device.

16. A non-transitory machine-readable storage medium storing instructions which, when executed, cause a processing device to:
  detect one or more user interactions by a first user with the wearable oral device, wherein the one or more user interactions comprise a first user interaction by the first user with the mouthpiece; and
  in response to detecting the one or more user interactions, perform one or more operations in view of the one or more user interactions, wherein the one or more operations comprise:
    presenting a first content item via the bone conduction component of the wearable oral device, wherein the first content item comprises audio content related to one or more of: the first user, physiological data of the first user, the point of interest; and
    sending, to a user device, a request for unlocking the user device, wherein the user device comprises a user application that causes the audio content to be presented to the first user via the bone conduction component, wherein the user application is programmed to access, retrieve, present, and navigate content served by a server, wherein the user application displays an embedded media player, wherein the user application detects the user interactions by the first user with the wearable oral device and determines that the user interactions indicate a search query, wherein the user application determines one or more search results based on the search query in view of the detected user interactions, wherein the user application sends a request for performing a search based on the search query to a server-side component of the server, wherein the server-side component generates the one or more search results and sends a response including the one or more search results to the user application;
    in view of the detection of the first user interaction and a determination that the wearable oral device is in a predetermined proximity to the point of interest, presenting media content related to the point of interest;
    wherein the user application enables communications between the first user and one or more other users, wherein the user application identifies the one or more other users that are related to the first user and presents content to facilitate communications between the first user and the one or more other users; and
    wherein the media content in view of the one or more user interactions by the first user with the wearable oral device comprises one or more content items related to a second user.

* * * * *